United States Patent [19]

Vermeer et al.

[11] Patent Number: 5,714,333
[45] Date of Patent: Feb. 3, 1998

[54] PROCESS FOR PREPARING CLEAR SERA WHICH ARE STABLE OVER A LONG PERIOD

[75] Inventors: Hans Vermeer, Lahntal-Gosselden; Tibor Toth; Gerhard Münscher, both of Marburg, all of Germany

[73] Assignee: Behring Diagnostics GmbH, Marburg, Germany

[21] Appl. No.: 365,019

[22] Filed: Dec. 28, 1994

[30] Foreign Application Priority Data

Dec. 29, 1993 [DE] Germany .................. 43 44 868.2

[51] Int. Cl.[6] .................. G01N 1/28; C07K 16/00
[52] U.S. Cl. .................. 435/7.1; 436/536; 530/387.1; 525/326.9; 526/264
[58] Field of Search .................. 530/387.1; 540/485; 525/326.9; 526/264; 435/7.1; 436/536

[56] References Cited

FOREIGN PATENT DOCUMENTS

| A3303083 | 8/1984 | European Pat. Off. . |
| 0 130 537 B1 | 1/1985 | European Pat. Off. . |
| 0 137 221 B1 | 4/1985 | European Pat. Off. . |
| 0 294 714 B1 | 12/1988 | European Pat. Off. . |
| A0294714 | 12/1988 | European Pat. Off. . |
| A0554657 | 8/1993 | European Pat. Off. . |
| 28 29 531 | 1/1980 | Germany . |

OTHER PUBLICATIONS

"Immunonephelometric Determination of Apolipoprotein A–1 in Hyperlipoproteinemic Serum", C. Heuck et al., Clin. Chem., 29(1): 120–125 (1983).

*Primary Examiner*—Frank C. Eisenschenk
*Attorney, Agent, or Firm*—Finnegan, Henderson, Farabow, Garrett & Dunner, L.L.P.

[57] ABSTRACT

The present invention relates to a process for preparing clear sera which are stable over a long period and also to their use in diagnostics.

15 Claims, 1 Drawing Sheet

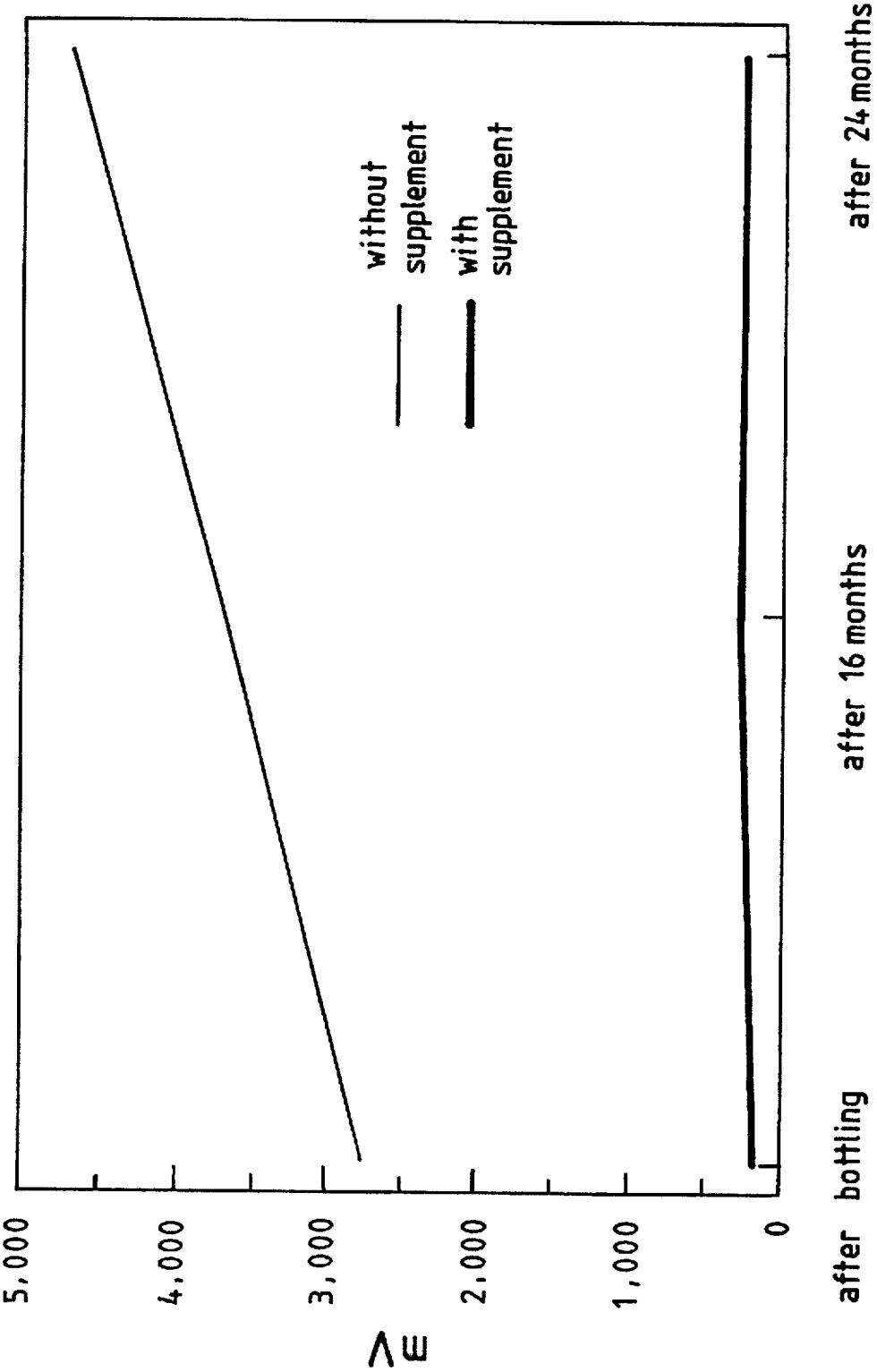

PROCESS FOR PREPARING CLEAR SERA WHICH ARE STABLE OVER A LONG PERIOD

FIELD OF THE INVENTION

The present invention relates to a process for preparing clear sera which are stable over a long period and also to their use in diagnostics.

BACKGROUND OF THE INVENTION

Owing to their high degree of specificity, their sensitivity and their rapidity, increasing use is being made of immunological methods of diagnosis. Of these methods, the precipitation methods for quantitatively determining serum proteins (radial immunodiffusion, nephelometry and turbidimetry) play a particularly important role. Because of their high degree of precision, their rapidity and their ability to be automated, nephelometric and turbidimetric determination methods have for some years now increasingly gained access to medical investigation laboratories. These methods make use of the property of antigens and/or antibodies of forming immune complexes with the corresponding partner in an immunochemical reaction. The formation of antigen/antibody complexes which begins once the two partners have been mixed can then, for example, be measured photometrically.

The quantitative determination of the serum proteins provides important clues for diagnosis and for assessing the course of diseases.

Very high demands are placed on the antisera which are used for diagnostics, for example in relation to serum proteins. Besides possessing a high concentration of specific antibodies, they must also possess a high degree of stability at different temperatures and a high degree of translucency. This also applies to standard sera and control sera. All these sera are collectively designated "sera" in that which follows.

A difficulty which arises when preparing such sera is that they contain labile components which have to be removed as far as possible during the preparation, as turbidities and flocculations can otherwise develop which then have to be filtered off or centrifuged down before using the sera.

Various methods have hitherto been proposed for removing turbidities in serum samples, but these methods are only of limited value, particularly in the case of animal antisera.

Thus, a process is described in Clin. Chem. 29, 120–125 (1983), for example, in which serum turbidities are removed by means of extracting by shaking with a mixture of organic solvents. This method requires an additional procedural step in which, particularly in the case of strongly lipaemic sera, inter alia, uncontrollable changes in the volume of the sample material can additionally take place, resulting in falsification of the measurement results. Finally, when this process is used it is also no longer possible to determine serum constituents which are removed wholly or in part during the extraction.

A further problem is the disposal of the extracting agent, particularly when this is a halohydrocarbon.

A series of selectively binding adsorbents, whose common feature is a hydrophilic matrix to which phenyl groups or alkyl groups are bonded, have also been employed for adsorbing the lipoproteins. Lipoprotein-binding adsorbents based on silicon dioxide, which are available commercially, for example under the name Aerosil®, have also been described.

EP 0 137 221 describes the removal of lipoproteins with the aid of polyhydroxymethylene. Polyanions such as dextran sulfate or heparin can also be used for precipitating in the presence of cations ($Mg^{2+}$ and $Mn^{2+}$). A disadvantage is that, for most applications, quantities of polyanions and metal ions remaining in the supernatant must be removed.

EP 0 294 714 describes the use of approximately 0.3% by weight of polyvinylpyrrolidone for preventing lyophilized control sera from clouding once they have been redissolved.

DE-A-28 29 531 uses a cationic surfactant for preventing interference in the immunochemical determination of a serum protein.

In EP 0 130 537, surface-active agents which are composed of a polyethoxylated triglyceride and n-alkanesulfonate, and also, where appropriate, a non-ionic or anionic surfactant, are added to a biological fluid (e.g. serum) to remove turbidities.

While the processes described can effect a certain remedial action, when carrying out photometric analyses, in the case of turbidities which have been elicited by chylomicrons and VLDL (very low density lipoprotein), it has been found that turbidities and flocculations develop time and again, particularly during storage for relatively long periods ($\geq 1$ year).

These turbidities can be caused by a very wide variety of factors, and it is evident that only some are caused by lipids and lipoproteins. Additional causes could, for example, be the immune complexes which arose during the immunization.

SUMMARY OF THE INVENTION

It was, therefore, the object of the invention to find a simple process and/or agent for preparing clear sera, in particular for the immunochemical determination of protein, which are stable over a long period.

It has been found, surprisingly, that the known disadvantages can be overcome if the sera [lacuna] with a compound of the formula (I)

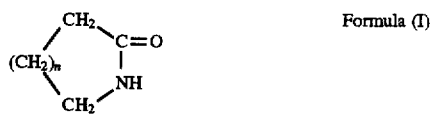

Formula (I)

n is 0–8, preferably n is 1 to 4.

These compounds, which are known per se to the person skilled in the art, belong to the cyclic carboxamides and are notable for a high dipole moment and very good dissolution properties. Butyrolactam (pyrrolidone), valerolactam and caprolactam are preferred representatives of this class of compounds.

This invention consequently relates to a process for preparing clear sera which are stable over a long period and which are used in diagnostics, a quantity of a compound of the formula (I) which is sufficient to prevent and/or eliminate a turbidity being added to the sera.

The compounds may be used on their own or in combinations. The combination of butyrolactam/caprolactam is particularly advantageous.

The compounds according to the invention are used in the main in concentrations of 0.2–30% by weight, preferably 1–10% by weight, particularly preferably of 1.5–3% by weight.

It can also be expedient to firstly dissolve the compounds according to the invention in a suitable aqueous solution and then add them to the sera. Such aqueous solutions are known per se to the person skilled in the art; examples of suitable solutions are an isotonic solution of sodium chloride or a 0.15 molar glycine/NaCl buffer solution/pH 7.2 to pH 10, preferably about pH 8.0. Tris, phosphate, borate/imidazole or acetate buffer solutions are also suitable.

Within the meaning of the invention, sera are also fractions which result during the purification of sera, in particular gamma globulin fractions as well.

The compounds according to the invention are particularly suitable for stabilizing animal antisera against human proteins, such as, for example, anti-human IgG (from rabbits), anti-$\alpha_2$-macroglobulin (from rabbits), anti-human IgM (from goats), anti-human albumin (from sheep), anti-$\alpha_1$-antitrypsin (from rabbits), anti-human apolipoprotein A-1 (from rabbits) or anti-human apolipoprotein B (from rabbits), or for standard sera and control sera of human origin which can contain, for example, rheumatoid factors and/or immune complexes.

The compounds according to the invention are preferably added to what is to a large extent a native antiserum in such a quantity that the concentration amounts to 0.2–30% by weight. Other known stabilizing substances, such as, for example, sodium azide or antibiotics, can also be added in addition. Once the compounds according to the invention have been added, the serum is preferably sterilized by filtration and then bottled under sterile conditions.

This invention furthermore relates to a serum for use in diagnostics, which serum contains a quantity of one or more compounds of the formula (I) which is effective in preventing and/or eliminating turbidities.

This invention also relates to the use of the sera according to the invention as standard sera and/or control sera in a diagnostic method. It is advantageous to use the sera according to the invention in diagnostic methods, such as, for example, radial immunodiffusion, nephelometry and turbidimetry, which are based on the principle of immunoprecipitation.

As is evident, inter alia, from FIG. 1, that the reagent without the supplement according to the invention exhibits a high blank value immediately after bottling, which value increases still further during the course of storage, whereas the reagent with the supplement according to the invention is clear and exhibits only a trivial rise in the blank value. The supplement according to the invention is also found to have a certain stabilizing effect, as can be gathered from Tab. 1.

Either a transmitted light signal or a scattered light signal can be used as the measure of turbidity. The turbidity in the reagent according to the invention preferably increases by less than 50%, during a storage period of 12 months. A serum is termed optically clear which, for example, under the conditions used in the examples, exhibits a scattered light signal of less than 1000, preferably less than 600 and particularly preferably less than 300 mV.

Within the meaning of the invention, stable over a long period means that the serum remains optically clear over a period of 12 months, preferably 24 months, during storage at, advantageously, 2°–8° C.

BRIEF DESCRIPTION OF THE DRAWING

FIG. 1 depicts the effect of supplement on the turbidity of serum initially and after prolonged storage.

DETAILED DESCRIPTION

The following examples illustrate the invention but in no way limit it.

Example 1 a) 1.5% by volume of 2-pyrrolidone ($\gamma$-butyrolactam) and 0.285 g of sodium azide were added to 300 ml of antiserum against human apolipoprotein A-I (from rabbits), and the antiserum was then sterilized by filtration. Following filter sterilization, the antiserum was bottled in 5 ml volumes under sterile conditions. The course of the standard curve did not alter after storage of the antiserum at from +2° to +8° C. over periods of 7, 16 and 24 months. All the bottled antiserum samples were clear.

300 ml of antiserum against human apolipoprotein A-I (from rabbits), but without 2-pyrrolidone ($\gamma$-butyrolactam), were sterilized by filtration as described under Example 1a), bottled and stored at from +2° to +8° C. The antiserum exhibited turbidity in all the bottles after only 7 months, and a nephelometric determination of apolipoprotein A-I was not possible without prior filtration.

The sera were tested by subjecting a standard series to nephelometric measurement. For this purpose, a standard serum was employed which contained 1,620 mg/l apolipoprotein A-I; the standard series was diluted from 1:5 to 1:160 using automated equipment, i.e. concentrations of from 324 to 10 mg/l were obtained. 10 µl of standard dilution together with 40 µl of antiserum against human apolipoprotein A-I were employed for the measurement.

TABLE 1

| | Scattered light signal (Bit) | | | | | |
|---|---|---|---|---|---|---|
| | after bottling | | after 16 months | | after 24 months | |
| | | | without supplement - after filtration | with supplement - without filtration | without supplement - after filtration | with supplement - without filtration |
| Standard dilution | without supplement | with supplement | | | | |
| 1:5 | 1,589 | 1,560 | 1,475 | 1,377 | 1,452 | 1,502 |
| 1:10 | 1,074 | 1,067 | 1,098 | 1,096 | 982 | 1,036 |
| 1:20 | 593 | 589 | 622 | 623 | 546 | 571 |
| 1:40 | 287 | 279 | 274 | 304 | 260 | 272 |
| 1:80 | 129 | 119 | 92 | 126 | 104 | 114 |
| 1:160 | 52 | 42 | 22 | 49 | 22 | 46 |
| Value without added serum | 2 | 2 | 13 | 0 | −1 | 2 |
| Value without added serum | 2 | 0 | 8 | 3 | 0 | 2 |

TABLE 1-continued

| | | | Scattered light signal (Bit) | | | |
|---|---|---|---|---|---|---|
| | | | after 16 months | | after 24 months | |
| | after bottling | | without supplement - after filtration | with supplement - without filtration | without supplement - after filtration | with supplement - without filtration |
| Standard dilution | without supplement | with supplement | | | | |
| Value without added serum AS blank value | 0 | −1 | −4 | 0 | 11 | 0 |
| mV opt. contr. | 2,750 turbidity | 160 clear | 3,700 turbidity | 280 clear | 4,700 turbidity | 270 clear |

Example 2 a) 3.0% by volume of 2-pyrrolidone (γ-butyrolactam) and 0.475 g of sodium azide were added to 500 ml of antiserum against human IgG (from rabbits), and the antiserum was then sterilized by filtration. Following filter sterilization, the antiserum was bottled in 5 ml volumes under sterile conditions. The course of the standard curve did not alter following storage of the antiserum at from +2° to +8° C. over a period of 28 months. All the bottled antiserum samples were clear.

b) 500 ml of antiserum against human IgG (from rabbits), but without 2-pyrrolidone (γ-butyrolactam), were sterilized by filtration as described under Example 2a), bottled and stored at from +2° to +8° C. After 2 years, the antiserum exhibited turbidity and flocculations in all the bottles and was no longer suitable for the nephelometric determination of IgG without being filtered once again.

The sera were examined by a standard series being subjected to nephelometric measurement. For this purpose, a standard serum containing 12,000 mg/l IgG was employed; the standard series was diluted from 1:80 to 1:2,560 using automated equipment, i.e. concentrations of from 150 to 4.6 mg/l were obtained. 100 μl of standard dilution together with 40 μl of antiserum against human IgG were employed for the measurement.

TABLE 2

| | Scattered light signal (Bit) | | | |
|---|---|---|---|---|
| | | | after 24 months | |
| | after bottling | | without supplement - after filtration | with supplement - without filtration |
| Standard dilution | without supplement | with supplement | | |
| 1:80 | 1,122 | 1,113 | 1,071 | 1,105 |
| 1:160 | 802 | 774 | 782 | 758 |
| 1:320 | 520 | 506 | 511 | 478 |
| 1:640 | 300 | 283 | 295 | 260 |
| 1:1,280 | 146 | 129 | 130 | 126 |
| 1:2,560 | 64 | 54 | 47 | 52 |
| Value without added serum | 0 | 2 | 4 | 1 |
| Value without added serum | 0 | 2 | 1 | 3 |
| Value without added serum | −1 | 2 | 3 | 0 |

TABLE 2-continued

| | Scattered light signal (Bit) | | | |
|---|---|---|---|---|
| | | | after 24 months | |
| | after bottling | | without supplement - | with supplement - |
| Standard dilution | without supplement | with supplement | after filtration | without filtration |
| AS blank value | | | | |
| mV opt. contr. | 600 clear | 270 clear | 1,600 turbidity | 340 clear |

Example 3 a) 1.5% by volume of 2-pyrrolidone (γ-butyrolactam) and 0.095 g of sodium azide were added to 100 ml of antiserum against human $\alpha_1$-antitrypsin (from rabbits), and the antiserum was sterilized by filtration. Following filter sterilization, the antiserum was bottled in 5 ml volumes under sterile conditions. The course of the standard curve did not alter after storage of the antiserum at from +2° to +8° C. over a period of 1 month. All the bottled antiserum samples were clear.

b) 100 ml of antiserum against human $\alpha_1$-antitrypsin (from rabbits), but without 2-pyrrolidone (γ-butyrolactam), were sterilized by filtration as described under Example 3a), bottled and stored at from +2° to +8° C. The antiserum exhibited turbidity and flocculations in all the bottles after only 1 month. It was only suitable for the nephelometric determination of $\alpha_1$-antitrypsin after renewed filtration.

The sera were examined by subjecting a standard series to nephelometric measurement. For this purpose, a standard serum was employed containing 1,650 mg/l $\alpha_1$-antitrypsin; the standard series was diluted from 1:5 to 1:160 using automated equipment, i.e. concentrations of from 330 to 10.3 mg/l were obtained. 20 μl of standard dilution together with 40 μl of antiserum against human $\alpha_1$-antitrypsin were employed for the measurement.

TABLE 3

| | Scattered light signal (Bit) | | | |
|---|---|---|---|---|
| | | | after 1 month | |
| | after bottling | | without supplement - after filtration | with supplement - without filtration |
| Standard dilution | without supplement | with supplement | | |
| 1:5 | 1,490 | 1,410 | 1,416 | 1,456 |
| 1:10 | 993 | 983 | 957 | 981 |
| 1:20 | 608 | 591 | 601 | 598 |
| 1:40 | 306 | 318 | 321 | 297 |
| 1:80 | 133 | 130 | 134 | 130 |
| 1:160 | 48 | 45 | 57 | 46 |
| Value without added serum | 0 | 0 | 10 | 1 |
| Value without added serum | 0 | 0 | 12 | 1 |
| Value without added serum AS blank value | 0 | 0 | 1 | 1 |
| mV | 160 | 120 | 5,430 | 250 |
| Bit | 7 | 16 | 412 | 13 |
| opt. contr. | clear | clear | turbidity | clear |

Example 4 a) 1.5% by volume of 2-pyrrolidone (γ-butyrolactam) and 0.095 g of sodium azide were added to 100 ml of antiserum against human $\alpha_1$-antitrypsin (from rabbits), and the antiserum was sterilized by filtration. Following filter sterilization, the antiserum was bottled in 5 ml volumes under sterile conditions. The course of the standard curve did not alter after storage of the antiserum at from +2° to 8° C. over a period of 6 months. All the bottled antiserum samples were clear.

b) 100 ml of antiserum against human $\alpha_1$-antitrypsin (from rabbits), but without 2-pyrrolidone (γ-butyrolactam), were sterilized by filtration as described under Example 4a), bottled and stored at from +2° to +8° C. The antiserum exhibited turbidity and flocculations in all the bottles after only 6 months. The standard curve could not be used for the $\alpha_1$-antitrypsin determination.

The sera were examined by subjecting a standard series to nephelometric measurement. For this purpose, a standard serum was employed containing 2,000 mg/l $\alpha_1$-antitrypsin; the standard series was diluted from 1:5 to 1:160 using automated equipment, i.e. concentrations of from 400 to 12.5 mg/l were obtained. 20 μl of standard dilution together with 40 μl of antiserum against human $\alpha_1$-antitrypsin were employed for the measurement.

TABLE 4

| | Scattered light signal (Bit) | | | |
|---|---|---|---|---|
| | | | after 6 months | |
| | after bottling | | without supplement - after filtration | with supplement - without filtration |
| Standard dilution | without supplement | with supplement | | |
| 1:5 | 1,670 | 1,705 | 1,685 | 1,806 |
| 1:10 | 1,264 | 1,276 | 1,214 | 1,350 |
| 1:20 | 841 | 855 | 817 | 887 |

TABLE 4-continued

| | Scattered light signal (Bit) | | | |
|---|---|---|---|---|
| | | | after 6 months | |
| | after bottling | | without supplement - after filtration | with supplement - without filtration |
| Standard dilution | without supplement | with supplement | | |
| 1:40 | 474 | 507 | 471 | 513 |
| 1:80 | 241 | 255 | 232 | 279 |
| 1:160 | 113 | 126 | 125 | 128 |
| Value without added serum | 0 | 2 | 57 | 14 |
| Value without added serum | 3 | 6 | 48 | 9 |
| Value without added serum AS blank value | 2 | 8 | 47 | 11 |
| mV | 60 | 100 | 11,140 | 280 |
| opt. contr. | clear | clear | turbidity | clear |

Example 5

1.5% of δ-valerolactam and 0.095 g of sodium azide were added to 100 ml of antiserum against human $\alpha_1$-antitrypsin (from rabbits), and the antiserum was sterilized by filtration, bottled and stored at from +2° to +8° C. After 6 months without the addition of the agent according to the invention, the antiserum exhibited massive flocculations, whereas the preparation containing added δ-valerolactam (prepared in accordance with the invention) was completely clear and without flocculations or turbidity.

Example 6 a) 1.5% by volume of 2-pyrrolidone (γ-butyrolactam) and 0.095 g of sodium azide were added to 100 ml of antiserum against human prealbumin (from rabbits), and the antiserum was sterilized by filtration. Following filter sterilization, the antiserum was bottled in 2 ml volumes under sterile conditions. The course of the standard curve did not alter after storage of the antiserum at from +2° to +8° C. over a period of 1 month. All the bottled samples were completely clear and without flocculations.

b) 100 ml of antiserum against human prealbumin (from rabbits), but without 2-pyrrolidone (γ-butyrolactam), were sterilized by filtration as described under Example 6a), bottled and stored at from +2° to +8° C. The antiserum exhibited substantial turbidity in all the bottles after only 1 month. It was only possible to use the antiserum for determining prealbumin once the flocculations had been removed by filtration.

The sera were examined by subjecting a standard series to nephelometric measurement. For this purpose, a standard serum was employed containing 310 mg/l prealbumin; the standard series was diluted from 1:2.5 to 1:80 using automatic equipment, i.e. concentrations of from 124 to 3.9 mg/l were obtained. 50 μl of standard dilution together with 40 μl of antiserum against human prealbumin were employed for the measurement.

TABLE 5

| | Scattered light signal (Bit) | | | |
|---|---|---|---|---|
| | after bottling | | after 2 months | |
| | | | without supplement - | with supplement - |
| Standard dilution | without supplement | with supplement | after filtration | without filtration |
| 1:2.5 | 1,283 | 1,257 | 1,275 | 1,278 |
| 1:5 | 995 | 970 | 978 | 975 |
| 1:10 | 620 | 612 | 612 | 615 |
| 1:20 | 339 | 332 | 347 | 335 |
| 1:40 | 183 | 167 | 189 | 168 |
| 1:80 | 84 | 71 | 95 | 78 |
| Value without added serum | 0 | 3 | 10 | 0 |
| Value without added serum | −1 | 0 | 12 | 1 |
| Value without added serum AS blank value | 2 | 1 | 9 | 3 |
| mV | 120 | 150 | 2,810 | 200 |
| Bit | 16 | 5 | 389 | 6 |
| opt. contr. | clear | clear | turbidity | clear |

Example 7 a) 3.0% by volume of 2-pyrrolidone (γ-butyrolactam) and 0.475 g of sodium azide were added to 500 ml of antiserum against human apolipoprotein B (from rabbits), and the antiserum was sterilized by filtration. After bottling in 5 ml volumes, the samples were stored at from +2° to +8° C. The samples exhibited neither turbidity nor flocculation after 3 years.

45.3 g of sodium azide were added to 47 710 ml of antiserum against human apolipoprotein B (from rabbits), and the antiserum was sterilized by filtration and bottled in 5 ml volumes. The bottled samples, which were stored at from +2° to +8° C., exhibited turbidity and flocculations after 30 months.

Example 8

Preparation of a control serum (human) for rheumatoid factors, anti-streptolysin O and CRP 50 ml samples of rheumatoid factor-positive serum (human) from each of 4 different donors were mixed. 19 ml of this serum pool, having a content of 674 IU/ml RF, were diluted with 81 ml of an isotonic solution of sodium chloride and 100 ml of a 1.8% solution of human γ-globulin having a content of approximately 1,800 IU/ml ASL (purity, at least 95%). 10 mg/ml of CRP, 0.2 g of sodium azide, 5 ml of butyrolactam and 0.4 g of benzamidinium chloride were then added. Following filter sterilization and bottling, samples were stored at from +2° to +8° C., at room temperature and at +37° C.

Without the addition of butyrolactam, the control serum exhibited flocculation after only 2 weeks, whereas the bottled samples to which butyrolactam had been added in accordance with the invention were completely clear and without flocculations after 6 months.

Example 9 a) 3.0% by volume of 2-pyrrolidone (γ-butyrolactam) and 0.475 g of sodium azide were added to 500 ml of antiserum against human $\alpha_2$-macroglobulin (from rabbits), and the antiserum was sterilized by filtration. After bottling in 5 ml volumes, the bottles were stored at from +2° to +8° C. The bottled samples are completely clear after 2, 5, 17 and 26 months.

b) 0.475 g of sodium azide was added to 500 ml of antiserum against human $\alpha_2$-macroglobulin (from rabbits), and the antiserum was sterilized by filtration. The bottled samples, which were stored as in Example 7a), exhibited turbidity and flocculations only 9 weeks after filter sterilization and bottling.

The sera were examined by subjecting a standard series to nephelometric measurement. For this purpose, a standard serum was employed containing 1,790 mg/l $\alpha_2$-macroglobulin; the standard series was diluted from 1:5 to 1:160 using automated equipment, i.e. concentrations of from 358 to 11.2 mg/l were obtained. 20 μl of standard dilution together with 40 μl of antiserum against human $\alpha_2$-macroglobulin were employed for the measurement.

TABLE 6

| | Scattered light signal (Bit) | | | | | |
|---|---|---|---|---|---|---|
| | after bottling | | after 6 months | | after 18 months | |
| | | | without supplement - | with supplement - | without supplement - | with supplement - |
| Standard dilution | without supplement | with supplement | after filtration | without filtration | after filtration | without filtration |
| 1:5 | 1,208 | 1,141 | 1,300 | 1,190 | 1,304 | 1,205 |
| 1:10 | 739 | 687 | 844 | 772 | 836 | 733 |
| 1:20 | 421 | 373 | 446 | 421 | 488 | 419 |
| 1:40 | 198 | 172 | 230 | 196 | 248 | 186 |
| 1:80 | 95 | 75 | 91 | 86 | 111 | 85 |
| 1:160 | 47 | 31 | 45 | 38 | 38 | 33 |
| Value without added serum | 6 | 1 | 1 | −6 | 7 | 1 |
| Value without added serum | 5 | 0 | 1 | 7 | 0 | 0 |
| Value without added serum | 16 | 0 | 2 | 4 | 0 | 0 |

TABLE 6-continued

| | | | Scattered light signal (Bit) | | | |
| --- | --- | --- | --- | --- | --- | --- |
| | | | after 6 months | | after 18 months | |
| | after bottling | | without supplement - after filtration | with supplement - without filtration | without supplement - after filtration | with supplement - without filtration |
| Standard dilution | without supplement | with supplement | | | | |
| AS blank value | | | | | | |
| mV | 1,400 | 140 | 7,460 | 170 | 3,860 90 | 190 27 |
| opt. contr. | clear | clear | turbidity | clear | turbidity | clear |

What is claimed is:

1. A process for preparing a clear serum which is stable over a long period and which is used in diagnostics, wherein a quantity of at least one compound of the formula (I)

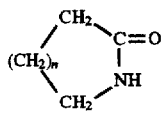

Formula I in which n is 0–8, which is sufficient to prevent and/or eliminate a turbidity is added to the serum.

2. The process as claimed in claim 1, wherein n is 1–4 in formula I.

3. The process as claimed in claim 1, wherein compounds of the formula (I) are added to the serum in such quantities that the concentration of these compounds in the serum is from 0.2 to 30% by weight.

4. The process as claimed in claim 1, wherein the compound of the formula (I) is butyrolactam.

5. The process as claimed in claim 1, wherein a mixture composed of at least 2 of the compounds of the formula (I) is added.

6. The process as claimed in claim 5, wherein butyrolactam and caprolactam are added.

7. The process as claimed in claim 1, wherein the serum is an antiserum.

8. The process as claimed in claim 1, wherein the serum is a standard serum and/or control serum.

9. A serum for use in diagnostics, which serum contains a quantity of one or more compounds of the formula (I) which is effective for preventing and/or eliminating turbidity.

10. The serum as claimed in claim 9, wherein the concentration of the compounds of the formula (I) is 0.2–30% by weight.

11. The serum as claimed in claim 9, wherein the concentration of the compounds of the formula (I) is 1–10% by weight.

12. The process as claimed in claim 1, wherein additional substances, known per se to the person skilled in the art, are added to the serum.

13. A method of preventing turbidity or flocculation in serum comprising the steps of:

a. adding a sufficient amount of a cyclic carboxamides of the formula (I)

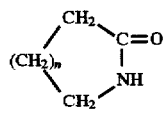

Formula I in which n is 0–8, to serum to prevent turbidity or flocculation; and b. recovering the serum of step (a).

14. A diagnostic method comprising the steps of:

a. adding a sufficient amount of a cyclic carboxamides of the formula (I)

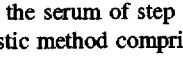

Formula I in which n is 0–8, to sera to prevent turbidity or flocculation;

b. diluting the sera of step (a) to form a standard dilution series;

c. subjecting the dilution series of step (b) to measurement to obtain a standard curve; and d. subjecting test samples to measurement.

15. A diagnostic method as claimed in claim 14, wherein the diagnostic method is a nephelometric or turbidimetric method.

* * * * *

UNITED STATES PATENT AND TRADEMARK OFFICE
CERTIFICATE OF CORRECTION

PATENT NO. : 5,714,333
DATED : February 03, 1998
INVENTOR(S) : Hans VERMEER et al.

It is certified that error appears in the above-identified patent and that said Letters Patent is hereby corrected as shown below:

Title Page, Item [75], in the Inventors, line 1, "Lahntal-Gosselden" should read --Lahntal-Gossfelden--.

Signed and Sealed this

Ninth Day of March, 1999

Attest:

Attesting Officer

Q. TODD DICKINSON

Acting Commissioner of Patents and Trademarks